United States Patent
Choi et al.

(10) Patent No.: US 9,495,078 B2
(45) Date of Patent: Nov. 15, 2016

(54) DISPLAY APPARATUS AND METHOD FOR MANAGING HEALTH

(71) Applicant: SAMSUNG ELECTRONICS CO., LTD., Suwon-si (KR)

(72) Inventors: Jun-sik Choi, Suwon-si (KR); Soo-yeoun Yoon, Seoul (KR); Bong-hyun Cho, Gwangju-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 200 days.

(21) Appl. No.: 13/753,914

(22) Filed: Jan. 30, 2013

(65) Prior Publication Data
US 2013/0212510 A1   Aug. 15, 2013

(30) Foreign Application Priority Data

Feb. 13, 2012 (KR) .................... 10-2012-0014487

(51) Int. Cl.
*G06F 3/048* (2013.01)
*G06F 3/0484* (2013.01)
*G06F 19/00* (2011.01)
*A61B 5/00* (2006.01)

(52) U.S. Cl.
CPC .......... *G06F 3/0484* (2013.01); *A61B 5/0077* (2013.01); *A61B 5/743* (2013.01); *A61B 5/748* (2013.01); *G06F 19/3475* (2013.01); *G06F 19/3481* (2013.01)

(58) Field of Classification Search
CPC ............... G06F 3/0484; G06F 19/3475; G06F 19/3481; A61B 5/743

USPC ......................................................... 715/771
See application file for complete search history.

(56) References Cited

U.S. PATENT DOCUMENTS

| | | | | |
|---|---|---|---|---|
| 5,262,815 A * | 11/1993 | Aumiller | .......................... | 396/2 |
| 7,328,119 B1 * | 2/2008 | Pryor et al. | .................. | 702/127 |
| 7,809,153 B2 * | 10/2010 | Bravomalo et al. | .......... | 382/100 |
| 2003/0027688 A1 * | 2/2003 | Gordon et al. | .................. | 482/9 |
| 2003/0108851 A1 * | 6/2003 | Posa | ............................. | 434/238 |
| 2003/0142951 A1 * | 7/2003 | Tsurugai et al. | ................ | 386/46 |

(Continued)

FOREIGN PATENT DOCUMENTS

WO     2005045748 A1    5/2005

OTHER PUBLICATIONS

Communication dated Apr. 29, 2013 from the European Patent Office in counterpart application No. 13153021.4.

*Primary Examiner* — William Bashore
*Assistant Examiner* — Gregory A DiStefano
(74) *Attorney, Agent, or Firm* — Sughrue Mion, PLLC

(57) ABSTRACT

A display apparatus and a method for managing health are provided. The display apparatus according to an exemplary embodiment includes a photographing unit which photographs a user image, a display unit which displays the photographed user image, a user interface unit which receives a user command regarding the displayed user image, and a controller which changes at least part of the displayed user image and displays the changed user image, and sets health management information corresponding to the displayed changed user image according to a user command. Accordingly, a user may set a goal for exercise and diet while watching a user image where a size has been changed, which is displayed on a display apparatus.

24 Claims, 7 Drawing Sheets

(56) References Cited

U.S. PATENT DOCUMENTS

2012/0254749 A1* 10/2012 Downs, III ............ G06Q 50/22
715/706

* cited by examiner

DISPLAY APPARATUS AND METHOD FOR MANAGING HEALTH

CROSS-REFERENCE TO RELATED APPLICATION

This application claims priority from Korean Patent Application No. 2012-0014487, filed in the Korean Intellectual Property Office on Feb. 13, 2012, the disclosure of which is incorporated herein by reference in its entirety.

BACKGROUND

1. Field

Aspects of exemplary embodiments relate to a display apparatus and a method for managing health, and more particularly, to a display apparatus which provides health management information using a user image and a method for managing health thereof.

2. Description of the Related Art

As modern society is getting westernized and industrialized, the number of people suffering from obesity has been increasing. Accordingly, various weight control methods such as dieting and exercising have been widely used. Although many ways to go on a diet are available, there are people who still fail to lose weight as much as they want.

The main reason for the failure of weight-control is lack of will power to lose weight. In order for a user to stay on a diet, he or she must be continuously motivated to lose weight. In the case of a general weight loss method, change of weight is monitored on a real time basis, and it is difficult to figure out how much weight has been lost in each part of the body.

In other words, it is difficult for a user to check the change of weight in each part of a body in relation to the amount of exercise he or she has been doing and, thus, the user may not be motivated to go on a diet as he or she feels less excited and satisfied.

SUMMARY

Aspects of the exemplary embodiments relate to a method which allows a user to manage health more efficiently.

A display apparatus according to an exemplary embodiment includes a photographing unit configured to photograph a user image, a display which displays the photographed user image, an interface unit which receives a command regarding the displayed user image, and a controller configured to change at least part of the displayed user image, display the changed user image, and set management information corresponding to the displayed user image according to the command.

The controller may display at least one from among the user image where a body part has been changed and the photographed user image according to the command.

The display apparatus may further include a storage, and the controller may calculate and display a calorie goal value related to the changed body part on a real time basis and store a calorie goal value selected by a user in the storage.

The calorie goal value may be calorie burn information corresponding to a degree of change of the changed body part.

The controller may set and display management information for each body part according to the calorie goal value for each body part stored in the storage, and store the set management information in the storage.

The management information may be a management program including at least one from among exercise course information, exercise time information, and a calorie burn information corresponding to an exercise time for the each body part.

The storage may store an exercise schedule table, and the controller may register and store the management program for each body part in the exercise schedule table according to an event. The event may be related to one from among a control command set by a user and an algorithm.

The storage may further store the user image photographed by the photographing unit, and the controller may measure a degree of calorie burn for each body part by comparing the user image stored in the storage unit with a user image currently photographed by the photographing unit and display exercise state information for each body part based on the measured degree of calorie burn.

The controller may renew management program information pre-stored in the storage based on the measured degree of calorie burn.

The command may be at least one from among a user motion and a control signal received from a remote controller.

The user image where the body part has been changed and the photographed user image may be displayed on one screen.

A method for managing health of a user on a display apparatus according to an exemplary embodiment includes photographing a user image, displaying the photographed user image, if a command regarding the displayed user image is received, changing at least part of the displayed user image and displaying a changed user image, setting management information corresponding to the displayed changed user image, and displaying the set management information.

The displaying the management information may include displaying at least one from among the user image where a body part has been changed and the photographed user image according to a command.

The setting the management information may include calculating and displaying a calorie goal value related to a changed body part on a real time basis and storing the calorie goal value selected by a user, in the storage unit.

The calorie goal value may be calorie burn information corresponding to a degree of change of the changed body part.

The setting the management information may include setting management information for each body part according to the calorie goal value for each body part stored in the storage unit, and storing the set management information in the storage unit.

The management information may be a management program including at least one from among the exercise course information, exercise time information, and a calorie burn information corresponding to an exercise time for the each body part.

The method may further include registering and storing the management program for each body part in the exercise schedule table stored in the storage unit according to a predetermined event.

The method may further include measuring a degree of calorie burn for each body part by comparing the user image stored in the storage unit with a user image currently photographed by the photographing unit and displaying exercise state information for each body part based on the measured degree of calorie burn.

The displaying the exercise state information may include renewing management program information pre-stored in the storage unit based on the measured degree of calorie burn.

The command may be at least one from among a user motion and a control signal received from a remote controller.

A display apparatus according to an exemplary embodiment includes a photographing unit configured to photograph a user image, a display which displays the photographed user image, an interface unit which receives a command regarding the displayed user image, and a controller configured to retrieve a stored user image which corresponds to the photographed user image, display the retrieved user image, and set management information corresponding to at least one from among the displayed photographed user image and the displayed retrieved user image, according to the command.

An apparatus according to an exemplary embodiment includes a photographing unit configured to photograph an image, a display which displays the photographed image, an interface unit which receives a command regarding the displayed image and a controller configured to change at least part of the displayed image, display the changed image, and set management information corresponding to the displayed image according to the command.

A method for managing health of a user on an apparatus according to an exemplary embodiment includes photographing an image, displaying the photographed image, if a command regarding the displayed image is received, changing at least part of the displayed image and displaying a changed mage, setting management information corresponding to the displayed changed image and displaying the set management information.

According to various exemplary embodiments, the display apparatus changes the size of a user image for each body part and displays the changed user image upon request from a user. Accordingly, the user may perform set a goal for exercise and diet while watching a user image where a size has been changed and thus, the user may be motivated to continue health management for each body part.

BRIEF DESCRIPTION OF THE DRAWINGS

The above and/or other aspects of exemplary embodiments will be more apparent with reference to the accompanying drawings, in which.

DETAILED DESCRIPTION

Figure 1:
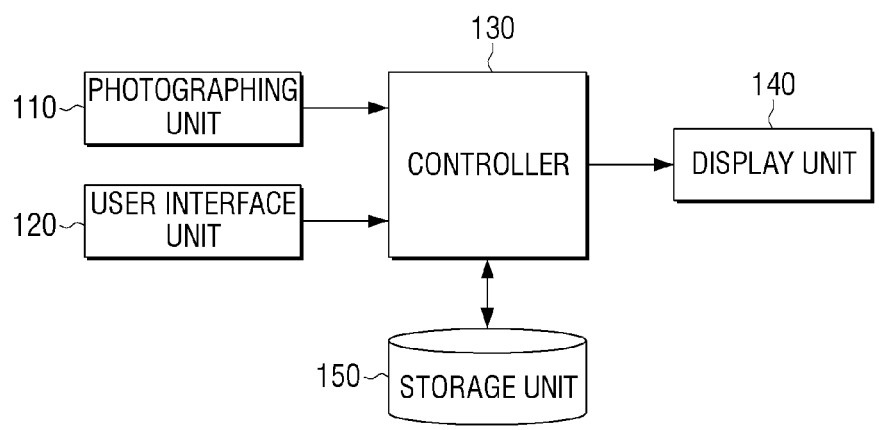
FIG. 1 is a block diagram of a display apparatus according to an exemplary embodiment.

Certain exemplary embodiments are described in higher detail below with reference to the accompanying drawings.

In the following description, like drawing reference numerals are used for the like elements, even in different drawings. The matters defined in the description, such as detailed construction and elements, are provided to assist in a comprehensive understanding of exemplary embodiments. However, exemplary embodiments can be practiced without those specifically defined matters. Also, well-known functions or constructions are not described in detail since they would obscure the application with unnecessary detail.

FIG. 1 is a block diagram of a display apparatus according to an exemplary embodiment.

As illustrated in FIG. 1, a display apparatus comprises a photographing unit 110, a user interface unit 120, a controller 130, and a display unit 140. The photographing unit 110 photographs a user image, and the user interface unit 120 receives a user command regarding a user image displayed through the display unit 140. The display unit 140 displays a user image photographed by the photographing unit 110 on a screen, and if a user command is received through the user interface unit 120, the controller 130 controls to effectuate the changes and displays at least part of a user image displayed on the screen through the display unit 140 and sets health management information corresponding to the user image which has been changed and displayed.

Specifically, the photographing unit 110 may be a camera which photographs an object. Accordingly, if a user manipulation command is input through the user interface unit 120, a user's body corresponding to the user manipulation command is focused and photographed. As such, if a user's body is photographed through the photographing unit 110, the display unit 140 displays a user image corresponding to the photographed user's body on the screen according to a control command from the controller 130. While a user image is being displayed on the screen, the user interface unit 120 may receive a command to change the size of a body part to be managed, from a user.

The user interface unit 120 may receive a user command regarding the size of a body part from a user motion sensed through the photographing unit 110 which photographs a user image, or may receive a user command regarding the size of a body part from a control signal received from a remote controller which is synchronized with the user interface unit 120. If a user command regarding the size of a body part is received through the user interface unit 120, the controller 130 changes and displays the size of a body part corresponding to the received user command from among body parts of a user image displayed on the screen. The controller 130 which changes a body part of a user image displayed on the screen according to a user command regarding the size of each body part will be explained in detail with reference to FIG. 2.

Figure 2:
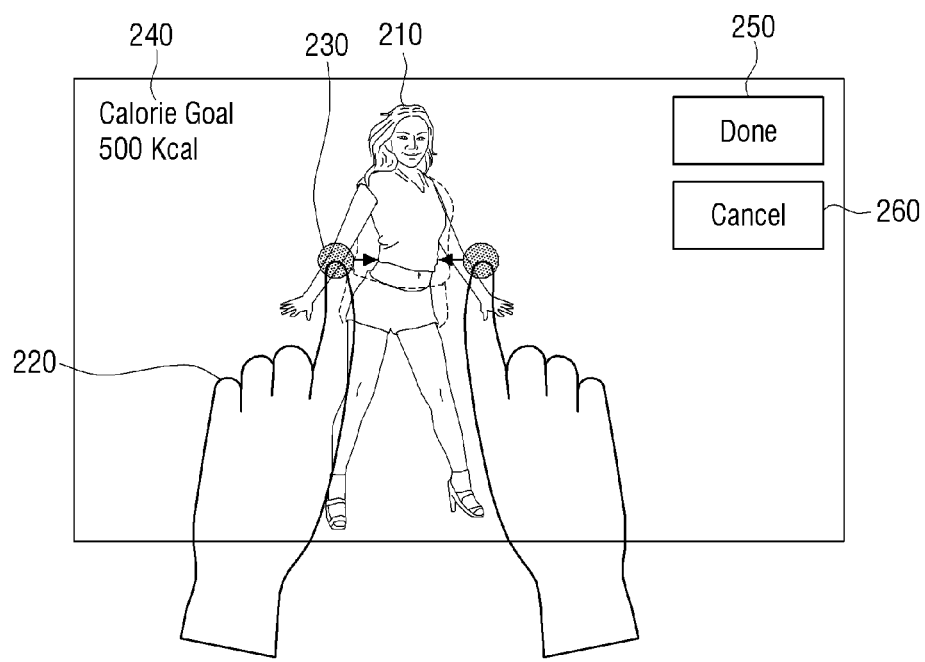
FIG. 2 is an exemplary view illustrating health management information using a user image on a display apparatus according to an exemplary embodiment.

FIG. 2 is an exemplary view illustrating health management information using a user image on a display apparatus according to an exemplary embodiment.

As illustrated in FIG. 2, the display unit 140 may display a user image 210 regarding a user's body which is photographed through the photographing unit 110. In an exemplary embodiment, a user may change the size of an upper body in the user image 210 displayed on the current screen using his or her own finger 220 while the user image 210 is being displayed on the screen. Specifically, a user may move his or her finger in an inward direction from a point 230 corresponding to an upper body part currently displayed on the screen. Accordingly, the photographing unit 110 may sense a user motion from the movement of the user's finger and receive a user command regarding change of size of each body part from the user motion sensed through the photographing unit 110.

In accordance with such a user command, the controller 130 changes the size of the upper body as much as the user's finger 220 moves in an inward direction. Accordingly, the display unit 140 may display on the screen the user image 210 including the upper body of which size has been changed as much as the difference between the dotted line and the solid line. Meanwhile, as illustrated in FIG. 3, the display unit 140 may display at least one of a user image where a body part is changed and an initial user image where a body part is not changed.

Figure 3:
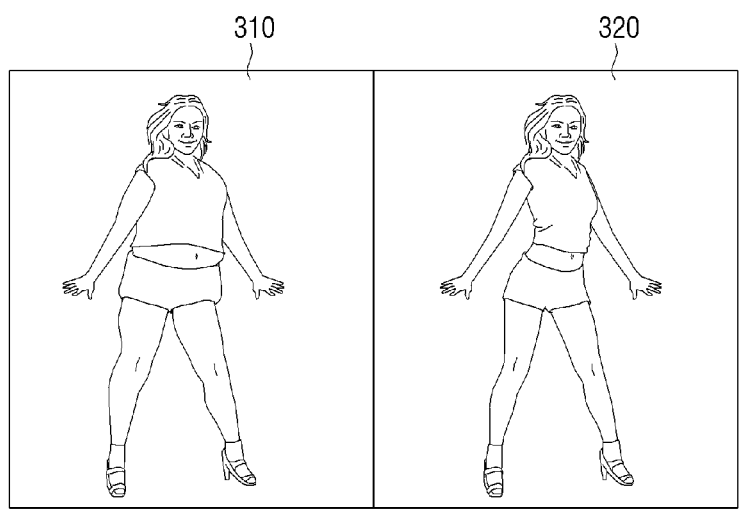
FIG. 3 is an exemplary view illustrating a user image on a display apparatus according to an exemplary embodiment.

FIG. 3 is an exemplary view illustrating a user image on a display apparatus according to an exemplary embodiment.

As illustrated in FIG. 3, the controller 130 may control to display at least one of a user image where a body part is changed and a user image photographed through the photographing unit 110 according to a user command. To be specific, if a user command regarding comparison of user images is input through the user interface unit 120, the controller 130 changes the sizes of two user images so that a user image where a body part is changed and a user image photographed through the photographing unit 110 are displayed on one screen.

If the sizes of two user images are changed, the display unit 130 displays a user image 310 photographed through the photographing unit 110 and a user image 320 where the size of a body part is changed on the screen. Accordingly, a user may determine whether to further change the changed user image 320 by checking the two user images 310, 320 displayed on the screen.

Meanwhile, the controller 130 which changes a body part of a user image in accordance with a user command related to changing a size for each body part may control the display unit 140 to set and display health management information corresponding to the changed body part. Herein, the health management information may include a goal calorie value regarding the changed body part, and the calorie goal value may relate to calories burned corresponding to the degree of change of the changed body part.

To be specific, the controller 130 changes a body part of a user image displayed on the screen in accordance with a user command regarding change of size for each body part, and calculates a calorie value corresponding to the changed body part on a real time basis. If a calorie goal value is calculated on a real time bases from the controller 130, the display unit 140 displays the calculated calorie goal value on the screen. Depending on an exemplary embodiment, a user may move his or her finger in an inward direction from the point 230 corresponding to an upper body part currently displayed on the screen using his or her finger 220. Accordingly, the photographing unit 110 may sense a user motion from the movement of the user's finger and receive a user command regarding change of size of each body part from the user motion sensed through the photographing unit 110.

In accordance with such a user command, the controller 130 changes the size of the upper body part in relation to how much the user's finger 220 moves in an inward direction. In this case, the controller 130 calculates a calorie goal value corresponding to the degree of change in size of the upper body part on a real time basis. For example, if a calorie goal value corresponding to the degree of change in size of the upper body is 500 Kcal, the display unit 140 displays a calorie goal value 240 of "Calorie Goal 500 Kcal" on the screen. Meanwhile, if another user command regarding change in size of the upper body is input through the user interface unit 120, the size of the upper body is changed again to the size corresponding to the other user command, and a calorie goal value corresponding to the changed size of the upper body will be set again. Accordingly, the display unit 140 may display a user image including the upper body which has been changed again by the controller 130 and a calorie goal value which has been set again on the screen.

Meanwhile, as illustrated in FIG. 2, the display unit 140 may display icons 250, 260 to receive an input regarding whether to select a calorie goal value on the screen. In an exemplary embodiment, if a command to select the icon 260 of "Cancel" is input through the user interface unit 120 while the calorie goal value 240 of "Calorie Goal 500 Kcal" is displayed, the controller 130 changes a user image currently changed and displayed on the screen to an initial user image. Accordingly, the display unit 140 may change the user image currently being displayed to the user image initially photographed, and display the changed user image on the screen.

Meanwhile, if a command to select the icon 260 of "Done" is input through the user interface unit 120, the controller 130 stores the user image which has been changed and displayed on the screen and the calorie goal value corresponding to the changed user image in the storage unit 150. Accordingly, the storage unit 150 may store a calorie goal value selected by a user and a user image corresponding to the calorie goal value.

Meanwhile, the controller 130 may control to set health management information according to a calorie goal value for each body part stored in the storage unit 150 and store the health management information in the storage unit 150. Herein, the health management information includes a calorie goal value as described above, and may further include at least one of exercise course information for each body part, exercise time information, and calorie burn information (e.g., an amount of calories burned) corresponding to exercise time. Accordingly, the controller 130 controls to set and store a health management program for each body part in the storage unit 150 in accordance with a calorie goal value for each body part stored in the storage unit 150, and controls the display unit 140 to display the health management program. As a result, the display unit 140 may display the health management program according to a calorie goal value for each body part on the screen.

Figure 4:
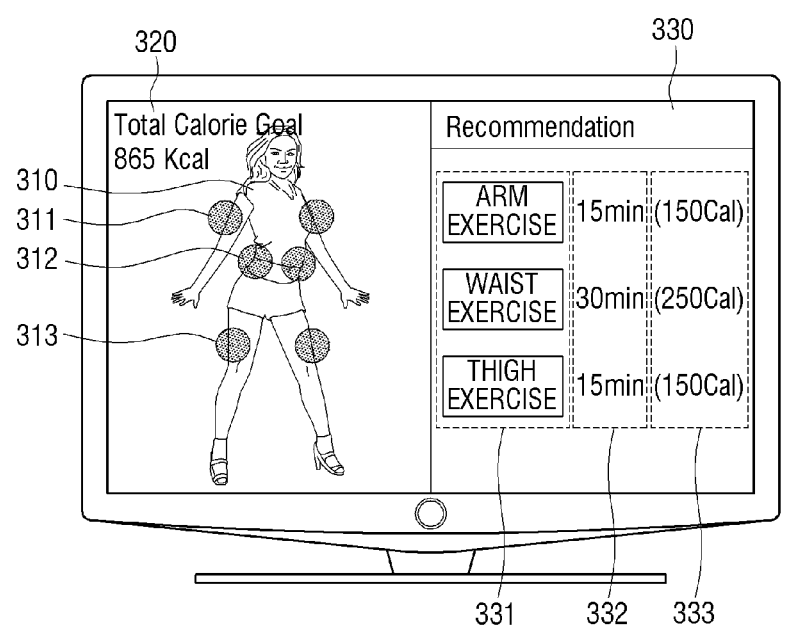
FIG. 4 is an exemplary view illustrating a health management program on a display apparatus according to an exemplary embodiment.

FIG. 4 is an exemplary view illustrating a health management program on a display apparatus according to an exemplary embodiment.

As illustrated in FIG. 4, the storage unit 150 may store a calorie value goal for each body part which has been changed by a user. For example, the storage unit 150 may store a calorie goal value regarding an arm, waist, and thigh. In this case, the controller 130 sets a health management program using a calorie goal value regarding the arm, waist, and thigh. Herein, the health management program 330 may include an exercise item 331, an exercise time 332, and calorie burn information 333 corresponding to an exercise time.

As described above, the storage unit 150 stores a calorie goal value regarding the arm, waist, and thigh and thus, the controller 130 may set the exercise item 331 which is included in the health management program 330 as an exercise item for the arm, waist, and thigh. In addition, the controller 130 may set the exercise time 332 corresponding to each of the arm exercise, waist exercise, and thigh exercise as 15 min, 30 min, and 15 min, respectively, and may set the calorie burn information 333 corresponding to each of the exercise time 332 as 150 Cal, 250 Cal, and 150 Cal, respectively. As such, if the health management program 330 is set in accordance with a calorie goal value for each body part stored in the storage unit 150 through the controller 130, the display unit 140 displays the set health management program 330 on the screen.

In this case, the display unit 140 displays the user image 310 in which the size of each body part has been changed on one side of the screen along with the health management program 330 according to a control command of the controller 130. As illustrated in the drawing, the health management program 330 related to the arm, waist and thigh is displayed and thus, the display unit 140 displays the user image 310 in which the size of the arm, waist and thigh has been changed on the screen along with the health management program 330. In this case, the display unit 140 displays identification icons 311, 312, 313 corresponding to the arm, waist and thigh, respectively, of which sizes have been changed from among body parts of the user image 310 displayed on the screen, and, thus, a user may check changed body parts more easily.

In addition, the display unit 140 may display the total calorie value goal 320 of "Total Calorie Goal 865 Kcal" on the upper end of the user image 310 displayed on the screen using a calorie goal value 320 regarding the arm, waist and thigh stored in the storage unit 150.

Meanwhile, depending on the additional aspects of exemplary embodiments, the storage unit 150 may store an exercise schedule table, and the controller 130 may register a health management program for each body part in an exercise schedule table stored in the storage unit 150 and store the health management program therein.

Figure 5:
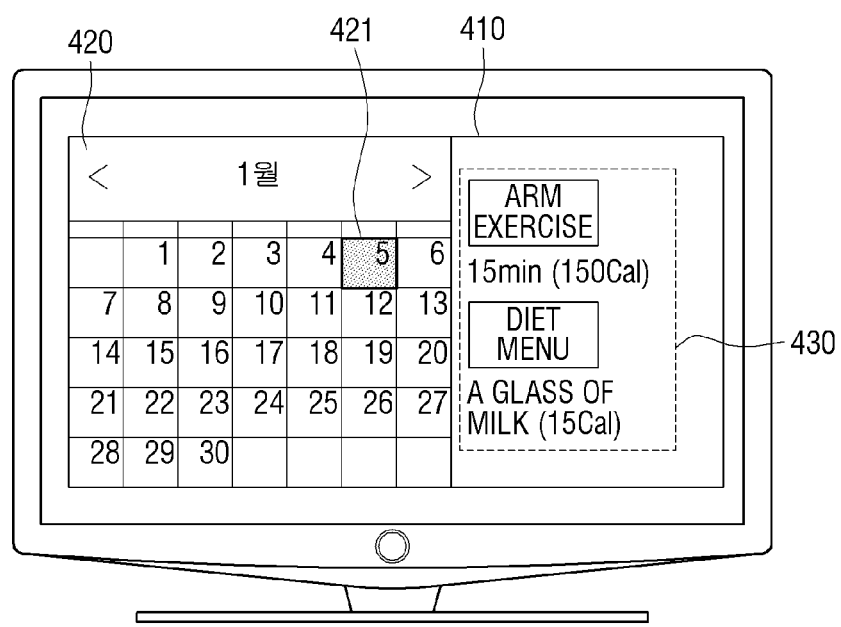
FIG. 5 is an exemplary view illustrating that a health management program is registered and stored in an exercise schedule table according to an exemplary embodiment.

FIG. 5 is an exemplary view illustrating that a health management program is registered and stored in an exercise schedule table according to an exemplary embodiment.

As illustrated in FIG. 5, the display unit 140 may display an exercise schedule table 410 where a health management program for each body part is registered on the screen. Specifically, the controller 130 may register a health management program in the exercise schedule table 410 according to a predetermined event. Herein, the predetermined event may be an event according to a control command set by a user or a set algorithm. As illustrated in FIG. 4, if a health management program regarding the arm, waist and thigh is set, the controller 130 may register the health management program regarding the arm, waist, and thigh in the exercise schedule table 410 according to a predetermined event. That is, the controller 130 may register the health management program regarding the arm, waist and thigh in the January schedule table 420 of the exercise schedule table 410.

For example, a health management program regarding the arm may be registered in the dates of 1, 5, 9, 13, 17, 21, 25, and 29 from among dates 1-31 of the January schedule table 420, a health management program regarding the waist may be registered in the dates 2, 6, 10, 14, 18, 22, 26, and 30, and a health management program regarding the thigh may be registered in the dates 3, 6, 11, 15, 19, 23, 27, and 31. Accordingly, the display unit 140 may provide a health management program registered for each day through an exercise schedule table. For example, if today is January 5, the display unit 140 highlights the 5$^{th}$ date from among the dates displayed on the January schedule table 420 of the exercise schedule table 410 and displays the health management program 420 regarding the arm registered on the 5$^{th}$ date on one side of the screen. As such, the display unit 140 displays a health management program including an exercise item, an exercise time, and calorie burn information corresponding to an exercise time regarding a body part corresponding to a date on one side of the screen. Accordingly, a user may adjust exercise and diet according to the health management program displayed on the screen.

Meanwhile, depending on additional aspects of exemplary embodiments, the storage unit 150 stores a user image photographed by the photographing unit 110, and the controller 130 compares the user image stored in the storage unit 150 with the user image currently photographed by the photographing unit 110 and measures the degree of calorie burn for each body part, in accordance with a user command regarding an exercise state. Subsequently, the controller 130 may control the display unit 140 to display exercise state information for each body part based on the measured degree of calorie burn. In addition, the controller 130 may renew a health management program for each body part pre-stored in the storage unit 150 based on the measured degree of calorie burn.

Specifically, while a user image of a user is stored in the storage unit 150, the photographing unit 110 photographs a user image regarding a body of the user according to a user command. Subsequently, if a user command regarding an exercise state is input through the user interface unit 120, the controller 130 obtains a user image related to a user image currently photographed through the photographing unit 110 from among a plurality of user images stored in the storage unit 150. According to an exemplary embodiment, the controller 130 may detect a face image from a user image currently photographed by the photographing unit 110 and obtain a user image matching with the detected face image from the storage unit 150. According to another exemplary embodiment, if a user command related to section of a user image is received, the controller 130 may obtain a user image corresponding to a user command from the storage unit 150.

Based on the above exemplary embodiment, if a user image related to a currently-photographed user image from among user images stored in the storage unit 150 is obtained, the controller 130 compares the obtained image with the user image which is currently photographed. Subsequently, the controller 130 obtains a health management program related to a user image in which a body part of the obtained user image is changed from the storage unit 150. Accordingly, the controller 130 measures calorie burn for each body part with reference to the obtained health management program. Specifically, the controller 130 measures the degree of change in calorie burn which is a calorie value goal by comparing a user image stored in the storage unit 150 with the currently-photographed user image with reference to the user image of which size has been changed.

Subsequently, the controller 130 determines whether an exercise state for each body part is normal based on the measured degree of change in calorie burn, and renews a health management program stored in the storage unit 150 according to the determined result. Meanwhile, the display unit 140 displays the exercise state information determined by the controller 130 on the screen and thus, a user may easily check whether the exercise for the body part that he or she changes has been done properly.

For example, the storage unit 150 may set and store a calorie value goal for the change of the size of the upper body as 500 Kcal. In this case, the controller 130 recalculates a calorie value goal for the upper body of a user image which is currently photographed with reference to the upper body of which size is changed. Subsequently, the controller 130 may renew a calorie value goal regarding the upper body stored in the storage unit 150 to the recalculated calorie value goal, and reset a health management program according to the renewed calorie goal value.

So far, the operation of managing health of a user by using an image on a display apparatus according to an exemplary has been explained in detail. Hereinafter, a method for managing health on a display apparatus according to an exemplary embodiment will be explained in detail.

Figure 6:
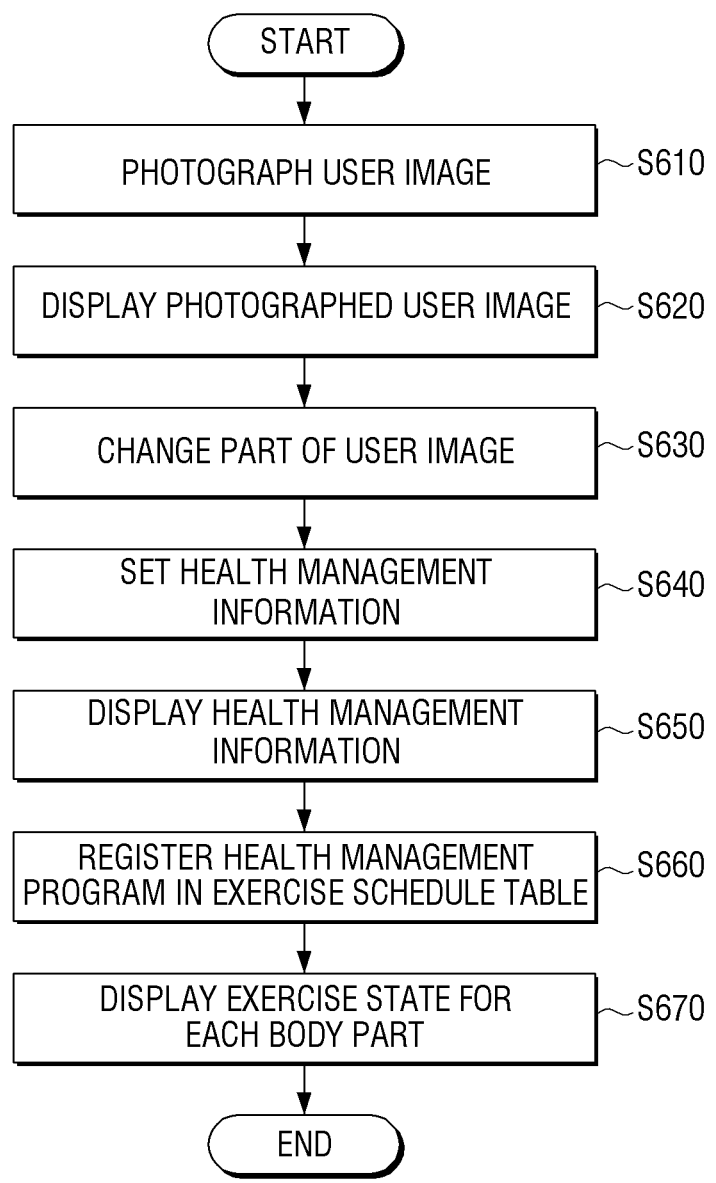
FIG. 6 is a flowchart illustrating a method for managing health using a user image on a display apparatus according to an exemplary embodiment.

FIG. 6 is a flowchart illustrating a method for managing health using a user image on a display apparatus according to an exemplary embodiment.

As illustrated in FIG. 6, a display apparatus photographs a user image regarding a user by using a camera provided in the display apparatus (S610). Subsequently, the display apparatus displays the photographed user image on the screen (S620). If a user command to change a size for each body part is received while the user image is displayed on the screen, the display apparatus changes and displays at least part of the user image corresponding to the user command (S630).

Specifically, the display apparatus may receive a user command regarding the change of size for each body part from a control signal received from a remote controller which is synchronized with a user motion or the display apparatus. If a user command regarding the change of size for the body part is received as a user motion, the display apparatus may sense the user motion from the movement of a user finger, and receive a user command regarding the change of size for body part from the sensed user motion.

Specifically, as explained above with reference to FIG. 2, a user may change the size of the upper body from among body parts of the actual image displayed on the current screen by using his or her own finger while the user image is displayed on the screen. For example, if the movement of a user finger in an inward direction is sensed at a point corresponding to the upper body displayed on the current screen, the display apparatus changes the size of the upper body as much as the user's finger moves in an inward direction. Accordingly, the display unit may display on the screen the user image including the upper body of which size has been changed as much as the difference between the dotted line and the solid line.

In this case, as illustrated in FIG. 3, the display apparatus may display at least one of a user image where a body part has changed and an initial image where a body part has not been changed. Specifically, if a user command regarding comparison of user images is input from a user, the display apparatus changes the size of two user images so that a user image where a body part has changed and an initially-photographed user image may be displayed on one screen, and displays the two user images of which the size of the images therein may be different, on the screen.

Accordingly, the user may compare the original user image with the user image where a body part has been changed with a single glance, and determine whether to further change the changed user image more easily.

As such, a display apparatus which changes and displays a body part of a user image according to a user command regarding the change of size for each body part sets health management information corresponding to a displayed user image and displays the health management information (S640, S650). Herein, the health management information includes a calorie value goal related to a changed body part and a health management program. In addition, the calorie value goal may be calorie burn information corresponding to the degree of change of the changed body part, and the health management program may include at least one of exercise course information for each body part, exercise time information, and calorie burn information corresponding to exercise time. The method for setting the health management information including descriptions related to the calorie value goal and the health management program will be explained in greater detail with reference to FIG. 7.

Figure 7:
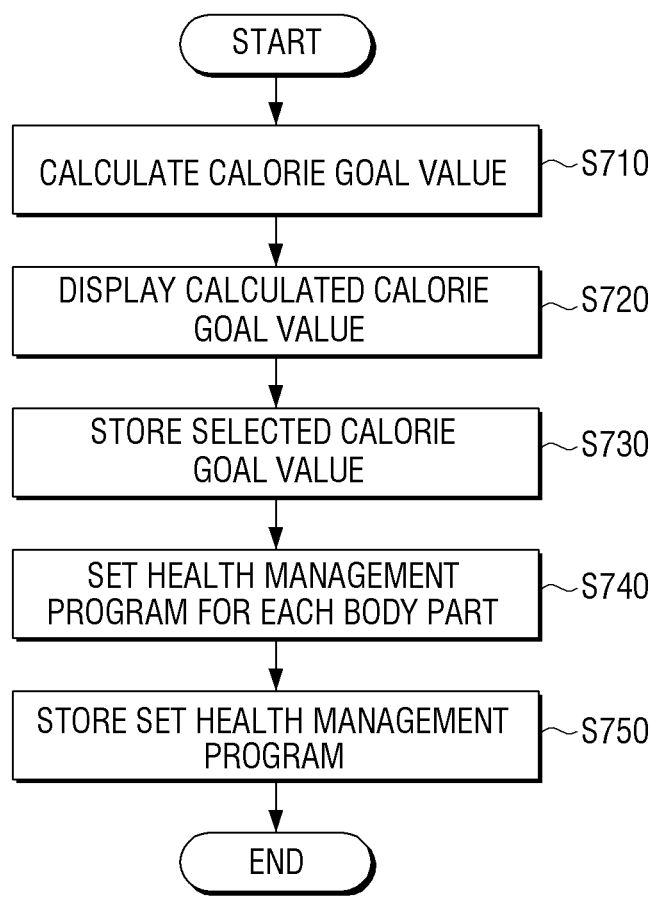
FIG. 7 is a flowchart illustrating a method for setting health management information corresponding to a changed body part on a display apparatus according to an exemplary embodiment.

FIG. 7 is a flowchart illustrating a method for setting health management information corresponding to a changed body part on a display apparatus according to an exemplary embodiment.

As illustrated in FIG. 7, if a user command regarding the change of size for each body part is received, a display apparatus changes a body part of a user image displayed on the screen and at the same time, calculates and displays a calorie goal value corresponding to the changed body part on a real time basis (S710, S720). Depending on an exemplary embodiment, as explained above with reference to FIG. 2, if a user motion is sensed from the movement of a user finger, the display apparatus may receive a user command regarding the change of size for the upper body from the sensed user motion. If such a user command is received, the display apparatus changes the size of the upper body and calculates a calorie goal value corresponding to the degree of the change of size for the upper body on a real time basis according to the received user command. For example, if a calorie goal value corresponding to the degree of change for the upper body is 500 Kcal, the display apparatus displays "Calorie Goal 500 Kcal" on the screen.

Meanwhile, if another user command regarding the change of size for the upper body is received while a calorie goal value is displayed on the screen, the display apparatus may again change the size of the upper body to a size corresponding to the other user command and reset a calorie goal value to correspond to the changed size for the upper body.

Meanwhile, if a calorie goal value displayed on the screen is selected by a user, the display apparatus stores the selected calorie goal value and a user image corresponding to the calorie goal value (S730). As such, a calorie goal value for each body part is stored, the display apparatus sets and stores an exercise management program for each body part according to the pre-stored calorie goal value for each body part, as explained above with reference to FIG. 4 (S740, S750).

For example, a calorie goal value for the arm, waist and thigh may be stored. In this case, the display apparatus sets a health management program using a calorie goal value regarding the arm, waist and thigh. Herein, the health management program may include information on an exercise item, exercise time, and calorie burn information corresponding to the exercise time. Accordingly, as illustrated in FIG. 4, the display apparatus may set an exercise item as arm training, waist exercise and thigh exercise. In addition, the display apparatus may set an exercise time corresponding to each of arm exercise, waist exercise and thigh exercise to 15 min, 30 min, and 15 min, respectively, and may set calorie burn information corresponding to each exercise time to 150 Cal, 250 Cal, and 150 Cal, respectively. As such, if a health management program for each body part is set, the display apparatus displays the health management program on the screen.

In this case, the display apparatus may display a user image of which size is changed for each body part and the entire calorie goal values which are set in accordance with the change of size for each body part on one side of the screen along with a health management program. In addition, the display apparatus may display identification icons on the arm, waist, and thigh of which size has been changed from among body parts of the user image displayed on the screen, respectively and thus, a user may check the body part of which size has been changed more easily.

Meanwhile, the display apparatus may register and store a health management program for each body part in an exercise schedule table according to a predetermined event (S660). Herein, the predetermined event may be an event by a control command set by a user or a set algorithm. As explained above with reference to FIG. 5, for example, if a health management program regarding the arm, waist, and thigh is set, the display apparatus may register the health management program regarding the arm, waist, and thigh in the January schedule table of the exercise schedule table.

That is, a health management program regarding the arm may be registered in the dates of 1, 5, 9, 13, 17, 21, 25, and 29 from among 1-31 of the January schedule table, a health management program regarding the waist may be registered in the dates 2, 6, 10, 14, 18, 22, 26, and 30, and a health management program regarding the thigh may be registered in the dates 3, 6, 11, 15, 19, 23, 27, and 31. Accordingly, the display unit may provide a health management program registered for each day through an exercise schedule table. For example, if today is January 5, the display unit highlights the $5^{th}$ date from among the dates displayed on the January schedule table of the exercise schedule table and displays the health management program regarding the arm registered on the $5^{th}$ date on one side of the screen.

As such, the display unit displays a health management program including an exercise item, an exercise time, and calorie burn information corresponding to an exercise time related to a body part corresponding to a date on one side of the screen. Accordingly, a user may adjust exercise and diet according to the health management program displayed on the screen.

Meanwhile, according to additional aspects of exemplary embodiments, the display apparatus stores a user image photographed through a camera and compares a pre-stored user image with the currently-photographed user image in accordance with a user command regarding an exercise state in order to measure the degree of calorie burn for each body part. Subsequently, the display apparatus may display exercise state information for each body part based on the measured calorie burn information and renew the pre-stored health management program according to the measured degree of calorie burn (S670).

Specifically, while a user image is pre-stored, the display apparatus photographs a user image related to a user body according to a user command. Subsequently, if a user command regarding an exercise state is received, the display apparatus obtains a user image regarding the currently-photographed user image from among a plurality of pre-stored user images. In an exemplary embodiment, the display apparatus may detect a face image from a currently-photographed user image and obtain a user image matching the detected face image from the plurality of pre-stored user images. In another exemplary embodiment, if a user command regarding selecting of a user image is received from a user, the display apparatus may obtain a user image corresponding to the user command from the plurality of pre-stored user images.

Through the above exemplary embodiments, if a user image related to a currently-photographed user image is obtained from among the plurality of pre-stored user images, the display apparatus compares the obtained user image with the currently-photographed user image. Subsequently, the display apparatus obtains a health management program which is stored in relation with a user image where a body part of the obtained user image has been changed. Accordingly, the display apparatus may measure the degree of calorie burn for each body part with reference to the obtained health management program. Specifically, the display apparatus measures the degree of change in calorie burn which is a calorie goal value by comparing the user image of which the size has been changed with the currently-photographed user image.

Subsequently, the display apparatus determines whether the exercise state of each body part is normal based on the degree of change in the measured calories burned, and renews the pre-stored health management program according to the determination result. In addition, the display apparatus displays the exercise state information which determines whether the exercise state is normal and thus, a user may easily check whether the exercise state for the body part he or she changed is normal.

So far, the present invention has been explained based on exemplary embodiments.

The foregoing embodiments and advantages are merely exemplary and are not to be construed as limiting the present invention. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A display apparatus, comprising:
a storage;
a photographing unit configured to photograph a user image; a display which displays the photographed user image;
an interface unit which receives a command regarding the displayed user image;
and a controller configured to control the display to display a user image which is changed from the displayed user image according to a user command,
wherein the changed user image is an image in which a specific body part of a user is changed, and
wherein the controller, in response to a user command with respect to a physical dimension of a first body part of the user image, being input, calculates, in real time, a goal value for exercise to change the physical dimension of the first body part, and displays body management information including the calculated goal value for exercise and a user image in which the physical dimension of the first body part is changed.

2. The display apparatus as claimed in claim 1, wherein the controller displays at least one from among the user image where the specific body part has been changed and the photographed user image, according to the command.

3. The display apparatus as claimed in claim 1, wherein the goal value is calorie burn information which corresponds to a degree of change of one of respective changed body parts.

4. The display apparatus as claimed in claim 1, wherein the controller sets and displays the health management information for each body part according to the goal value for each body part stored in the storage, and stores the set health management information in the storage.

5. The display apparatus as claimed in claim 4, wherein the health management information is a health management program including at least one from among exercise course information, exercise time information, and calorie burn information corresponding to an exercise time for the each body part.

6. The display apparatus as claimed in claim 5, wherein the storage stores an exercise schedule table,
wherein the controller registers and stores the health management program for each body part in the exercise schedule table according to an event.

7. The display apparatus as claimed in claim 4, wherein the storage further stores the user image photographed by the photographing unit, and
wherein the controller measures a degree of calorie burn for each body part by comparing the user image stored in the storage with a user image currently photographed by the photographing unit and displays exercise state information for each body part based on the measured degree of calorie burn.

8. The display apparatus as claimed in claim 7, wherein the controller renews health management program information pre-stored in the storage based on the measured degree of calorie burn.

9. The display apparatus as claimed in claim 1, wherein the command is at least one from among a user motion and a control signal received from a remote controller.

10. The display apparatus as claimed in claim 2, wherein the user image where the body part has been changed and the photographed user image are displayed on one screen at a same time.

11. The display apparatus as claimed in claim 6, wherein the event is related to one from among a control command set by a user and an algorithm.

12. The apparatus as claimed in claim 1, wherein the controller, in response to a user command with respect to a second body part out of the user image being input, calculates, in real time, a goal value for exercise to change the second body part, and displays body management information including the calculated goal value for exercise and a user image in which the second body part is changed.

13. A method for managing health of a user on a display apparatus, the method comprising:
photographing a user image;
displaying the photographed user image;
if a command regarding the displayed user image is received, changing at least part of the displayed user image and displaying a changed image;
setting health management information corresponding to the displayed changed user image,
wherein the changed user image is an image in which a specific body part of the user is changed, and
wherein the setting the health management information comprises:
in response to a user command with respect to a physical dimension of a first body part of the user image, being input, calculating, in real time, a goal value for exercise to change the physical dimension of the first body part, and displaying body management information including the calculated goal value for exercise and a user image in which the physical dimension of the first body part is changed.

14. The method as claimed in claim 13, wherein the displaying the health management information comprises displaying at least one from among the user image where the specific body part has been changed and the photographed user image according to a command.

15. The method as claimed in claim 13, wherein the calorie goal value is calorie burn information corresponding to a degree of change of respective changed body parts.

16. The method as claimed in claim 13, wherein the setting the health management information comprises:
setting health management information for each body part according to the calorie goal value for each body part stored in the storage unit; and
storing the set health management information in the storage unit.

17. The method as claimed in claim 16, wherein the health management information is a health management program including at least one from among exercise course information, exercise time information, and calorie burn information corresponding to an exercise time for the each body part.

18. The method as claimed in claim 17, further comprising:
registering and storing the health management program for each body part in the exercise schedule table stored in the storage unit according to an event.

19. The method as claimed in claim 16, further comprising:
measuring a degree of calorie burn for each body part by comparing the user image stored in the storage unit with an user image currently photographed by the photographing unit and displaying exercise state information for each body part based on the measured degree of calorie burn.

20. The method as claimed in claim 19, wherein the displaying the exercise state information comprises renewing health management program information pre-stored in the storage unit based on the measured degree of calorie burn.

21. The method as claimed in claim 13, wherein the command is at least one from among a user motion and a control signal received from a remote controller.

22. The method as claimed in claim 14, wherein the user image where the body part has been changed and the photographed user image are displayed on one screen at a same time.

23. The method as claimed in claim 18, wherein the event is related to one from among a control command set by a user and an algorithm.

24. The method as claimed in claim 13, further comprising:
in response to a user command with respect to a second body part of the user image, being input, calculating, in real time, a goal value for exercise to change the second body part, and displaying body management information including the calculated goal value for exercise and a user image in which the second body part is changed.

* * * * *